(12) United States Patent
Johnston

(10) Patent No.: US 7,771,434 B2
(45) Date of Patent: Aug. 10, 2010

(54) BONE DISTRACTOR APPARATUS

(75) Inventor: Thomas S. Johnston, Jacksonville, FL (US)

(73) Assignee: KLS-Martin, LP, Jacksonville, FL (US)

( * ) Notice: Subject to any disclaimer, the term of this patent is extended or adjusted under 35 U.S.C. 154(b) by 555 days.

(21) Appl. No.: 11/246,769

(22) Filed: Oct. 7, 2005

(65) Prior Publication Data

US 2006/0079902 A1    Apr. 13, 2006

Related U.S. Application Data

(60) Provisional application No. 60/617,507, filed on Oct. 8, 2004.

(51) Int. Cl.
- *A61B 17/60* (2006.01)
- *A61B 17/66* (2006.01)
- *A61F 5/04* (2006.01)

(52) U.S. Cl. .................. 606/105; 606/57; 606/282; 606/90

(58) Field of Classification Search .............. 606/105, 606/57, 282, 90, 105.5
See application file for complete search history.

(56) References Cited

U.S. PATENT DOCUMENTS

| | | | | |
|---|---|---|---|---|
| 4,662,371 A | * | 5/1987 | Whipple et al. | 606/170 |
| 5,769,850 A | * | 6/1998 | Chin | 606/53 |
| 5,860,994 A | * | 1/1999 | Yaacobi | 606/166 |
| 5,893,879 A | * | 4/1999 | Hirshowitz et al. | 606/218 |
| 5,895,387 A | * | 4/1999 | Guerrero et al. | 606/71 |
| 6,716,218 B2 | * | 4/2004 | Holmes et al. | 606/105 |
| 6,786,910 B2 | * | 9/2004 | Fichtner et al. | 606/71 |
| 2002/0116002 A1 | * | 8/2002 | Sellers | 606/71 |
| 2005/0200608 A1 | * | 9/2005 | Ulla et al. | 345/168 |

\* cited by examiner

*Primary Examiner*—Thomas C Barrett
*Assistant Examiner*—Sameh Boles
(74) *Attorney, Agent, or Firm*—Thomas C. Saitta

(57) ABSTRACT

An improved distractor apparatus of the type having at least a pair of opposing bone plates secured distally and proximally to a pair of bone segments created by cutting an osteotomy gap, wherein the mounting brackets for securing the bone plates to the distractor means comprise abutment members that extend into the gap and abut the exposed ends of the two bone segments, such that distraction force is transferred to the bone segments by both the bone plates and the abutment members, wherein at least the abutment member on the distal mounting bracket is collapsible in the distal direction.

23 Claims, 4 Drawing Sheets

BONE DISTRACTOR APPARATUS

This application claims the benefit of U.S. Provisional Patent Application Ser. No. 60/617,507, filed Oct. 8, 2004.

BACKGROUND OF THE INVENTION

The invention is a bone distractor apparatus used during osteotomy procedures wherein a bone, such as the mandible for example, is to be lengthened by separating the bone into two segments, allowing bone regeneration to begin within the osteotomy gap, then slowly expanding the gap incrementally over time such that the bone is gradually extended to its desired length and the gap is completely filled with regenerated bone, a process referred to as osteogenesis or osteosynthesis. The bone distractor is a generally elongated device that comprises a mechanism, such as a threaded rod contained within a tubular housing, the rod being in connection with one or two movable shoe or mounting bracket members to which are connected a proximal bone plate and a distal bone plate, whereby the bone plates affixed on either side of the osteotomy gap to the bone to be extended can be gradually separated in a controlled and precise manner by rotating the threaded rod.

Often the distractor and mounting brackets are composed of metal, while the bone plates and bone screws are composed of a resorbable material, such that they will degrade and decompose within the body such that removal is not required. Because the distractor and mounting brackets often will not be removed until the bone plates and bone screws have seriously degraded, it is possible to remove and extract the distractor and mounting brackets from the patient by tearing the metal components from the resorbable components, which is accomplished by pulling the distractor generally in the axial direction through the surrounding tissue.

In an embodiment of interest, the metal mounting brackets are provided with abutment members that extend generally perpendicularly to the major plane containing the bone plates, such that the abutment members can be positioned against the ends of the bone segments which were created by the osteotomy. The abutment members provide a means to transfer the distraction force to the bone segments in addition to the bone screws that secure the bone plates to the bones, which is particularly desirable as the resorbable bone screws and bone plates weaken over time. Typically, the abutment members comprise relatively short arm or hook members.

The presence of these abutment members means alters slightly the technique for removing the distractor and the mounting brackets, since the distractor must now first be pulled slightly away from the bone segments or levered using the distal end as a fulcrum in a direction generally perpendicular to the axial direction in order for the abutment members to clear the bone during the axial extraction step. The abutment members, extending generally perpendicularly to the axial direction, increase damage to the tissue surrounding the distractor and mounting plates when withdrawn in the axial direction, especially for the abutment member on the distal bone plate, which is more difficult to access and manipulate during the extraction process.

It is an object of this invention to address the problems created during the distractor extraction process by the generally perpendicular abutment members, and in particular the distal abutment member, by structuring at least the distal member such that it is able to collapse in the distal direction so as to lie adjacent the mounting bracket or at least present a much reduced profile in the axial direction, whereby damage to the tissue surrounding the distractor and mounting bracket or brackets is significantly reduced when the distractor is pulled in the generally axial direction during removal.

BRIEF SUMMARY OF THE INVENTION

The invention is in general a bone distractor apparatus that incrementally separates bone segments that have been created by an osteotomy such that bone may regenerate in the osteotomy gap to produce a unified and lengthened bone. The bone distractor apparatus comprises distractor means incorporating a mechanism for increasing the distance between two bone plates that are adapted for fixation to the bone segments on opposite sides of the osteotomy gap. A representative and common mechanism is the combination of a threaded rod within a tubular housing, whereby rotation of the rod separates the bone plates, one of which is joined to the rod and the other to the end of the housing. The bone plates are typically fastened to the bone segments using bone screws.

In order to better disperse the stresses inherent in the distraction process, relatively short abutment members are provided so as to abut exposed ends of the bone segments. The abutment members, short tabs or arms, extend into the osteotomy gap generally perpendicularly to the bone plates and distractor means, such that some of the distraction force is applied to the ends of the bone segments as well as through the affixed bone plates.

It being desirable to minimize the damage to the tissue surrounding the bone during removal of the bone distractor apparatus, it is known to form the bone plates and bone screws of bio-resorbable material, such that the plates and screws may be left in the patient until they are eventually resorbed. In this case, the distractor means is typically removed by pivoting it outwardly against its distal end, such that it separates from the screws and plates. The elongated distractor means is then removed in the axial direction.

The presence of perpendicularly aligned abutment members increases the size of the bore in the tissue when the distractor means is moved axially, especially with regard to the distal abutment member. In this invention, at least the distal abutment member is mounted in a hinged manner such that it is able to pivot toward the distraction means in the distal direction, whereby a much smaller profile is presented when the distractor means is withdrawn through the tissue. In addition, the proximal abutment member may also be mounted in a hinged manner such that it may pivot in the distal direction, where a locking means is used to secure the proximal abutment member in perpendicular alignment until released for removal.

DETAILED DESCRIPTION OF THE INVENTION

Figure 1:
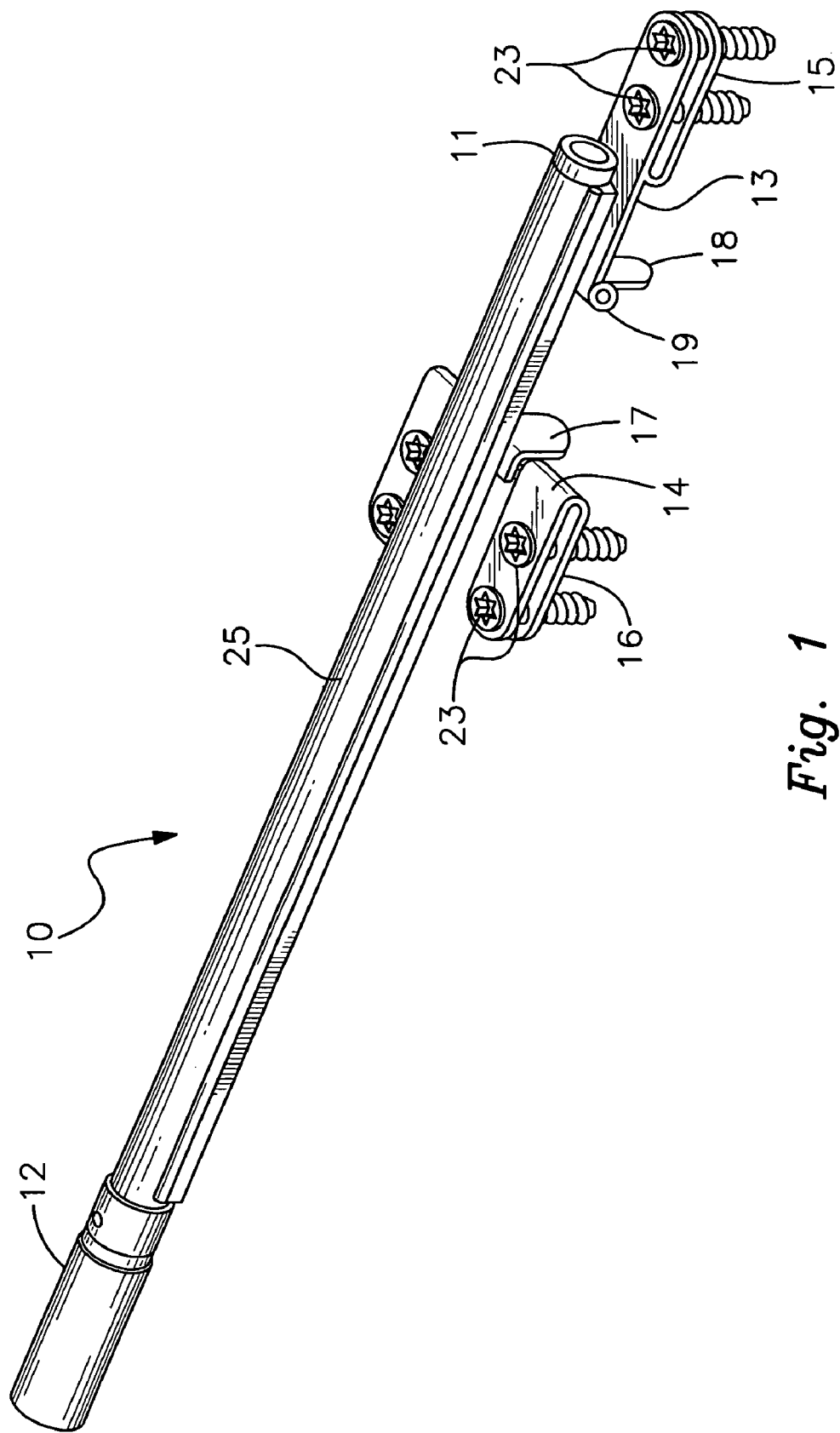
FIG. 1 is a perspective view of a distractor means having two mounting brackets adapted to retain bone plates, the mounting brackets connected in a manner such that the mounting members can be separated by operation of the distractor mechanism, and showing the abutment members in the generally perpendicular position.
Figure 2:
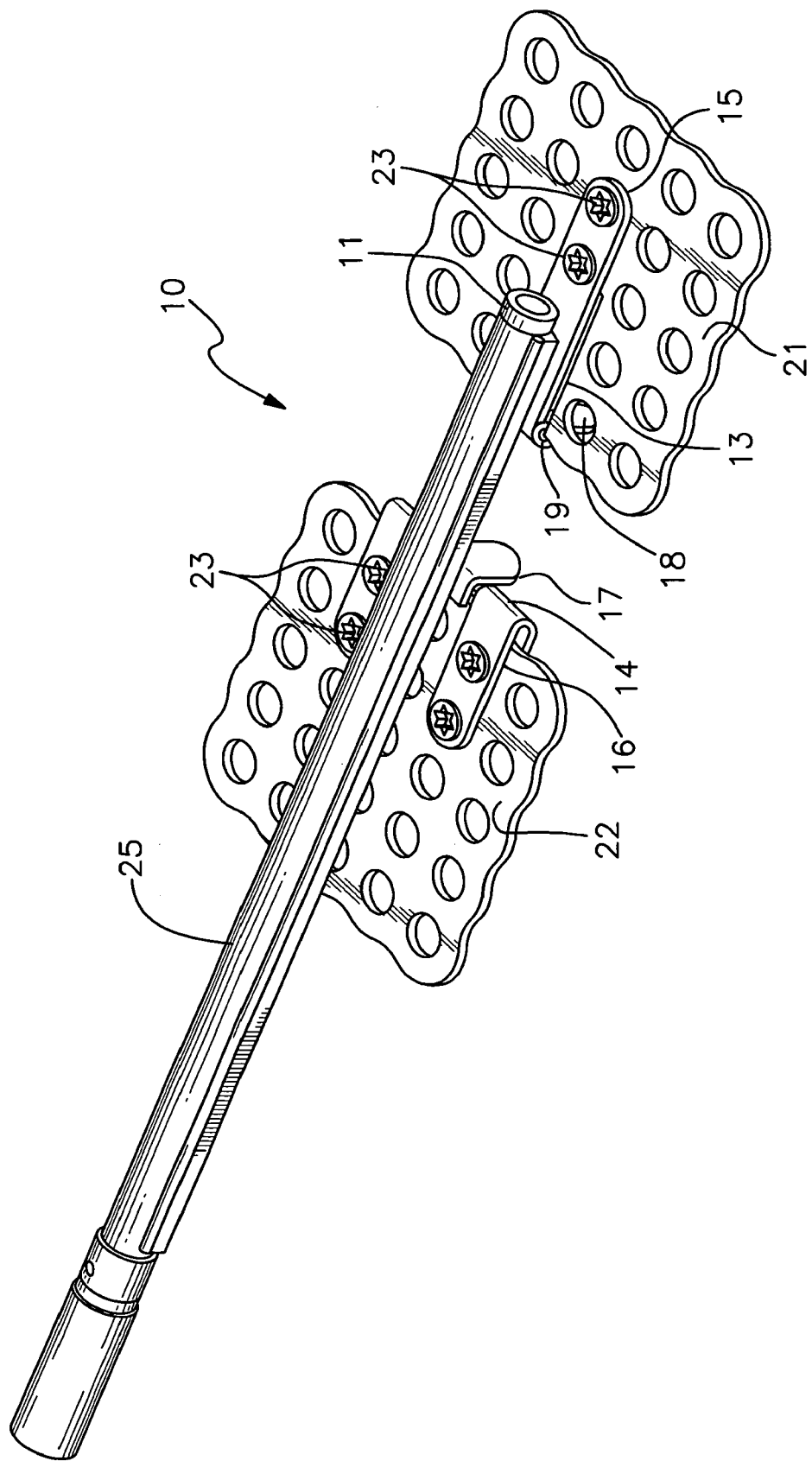
FIG. 2 is a perspective view similar to FIG. 1, showing the distal and proximal bone plates connected to the mounting brackets.
Figure 3:
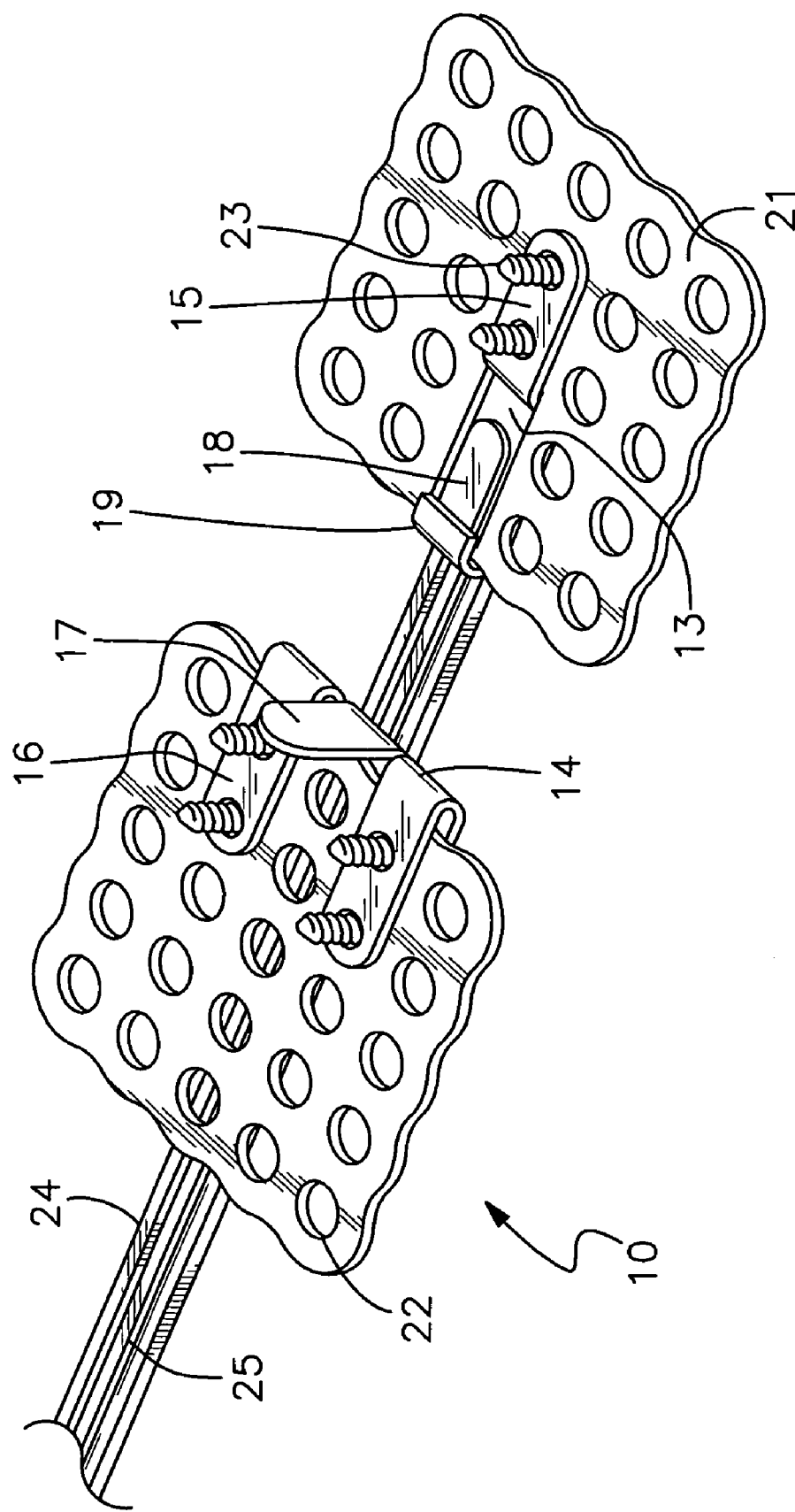
FIG. 3 is a perspective view of the underside of the distal and proximal bone plates, showing the distal abutment member in the collapsed position for removal of the distractor means and mounting brackets.

With reference to the drawings, the invention will now be described in detail with regard for the best mode and the preferred embodiment. In general, the invention is an improved distractor apparatus of the type having at least a pair of opposing bone plates secured distally and proximally to a pair of bone segments created by cutting an osteotomy gap, wherein the mounting brackets for securing the bone plates to the distractor means comprise abutment members that extend a short distance into the gap and abut the exposed ends of the two bone segments, such that distraction force is transferred to the bone segments by both the bone plates and the abutment members.

The invention comprises a distractor means 10 that incorporates a mechanism whereby, when the apparatus is secured to a proximal bone segment 98 and a distal bone segment 99 of a bone across an osteotomy gap 97, the bone segments 98 and 99 can be gradually separated during bone regeneration, such that the bone itself is lengthened as regenerated bone 96 fills the osteotomy gap 97. A typical or representative operative mechanism for the distractor means 10 known in the art comprises a threaded rod (not shown) rotatably disposed within an elongated tubular housing 25, the distractor means 10 having a distal end 11 and a proximal end 12, whereby the distractor means 10 is positioned on the patient such that the proximal end 12 remains relatively readily accessible to the physician. Other operative mechanisms may also be utilized without departing from the scope of the invention. The elongated housing 25 is provided with an axial slot 24, such that a proximal plate-mounting means 14 is in communication with the threaded rod so that rotation of the threaded rod results in movement of the proximal plate-mounting means 14 in the proximal axial direction. Alternatively, a housing need not be present and the proximal plate-mounting means 14 may be provided with a short internally threaded sleeve that encircles the threaded rod. A distal plate-mounting means 13 is either affixed to the distal end 11 of the distractor means housing 25 or is connected in communication with the threaded rod in a manner such that rotation of the threaded rod results in movement of the distal plate-mounting means 13 in the distal axial direction. Thus, actuation of the distractor means 10 increases the distance between the proximal plate-mounting means 14 and the distal plate-mounting means 13.

The distal plate-mounting means 13 as shown comprises a distal bracket member 15, shown as a generally U-shaped clip member, to receive a distal bone plate 21, and the proximal plate-mounting means 14 comprises a proximal bracket member 16, shown as a pair of U-shaped clip members, to receive a proximal bone plate 22, whereby the bone plates 21 and 22 are secured to the bracket members 15 and 16, respectively, and to the bone segments 98 and 99 by bone screws 23 inserted through apertures in the bracket members 15 and 16 and in the bone plates 21 and 22. The bone plates 21 and 22 and the bone screws 23 are most preferably composed of a bio-resorbable material, such material being well known in the art.

Figure 4:
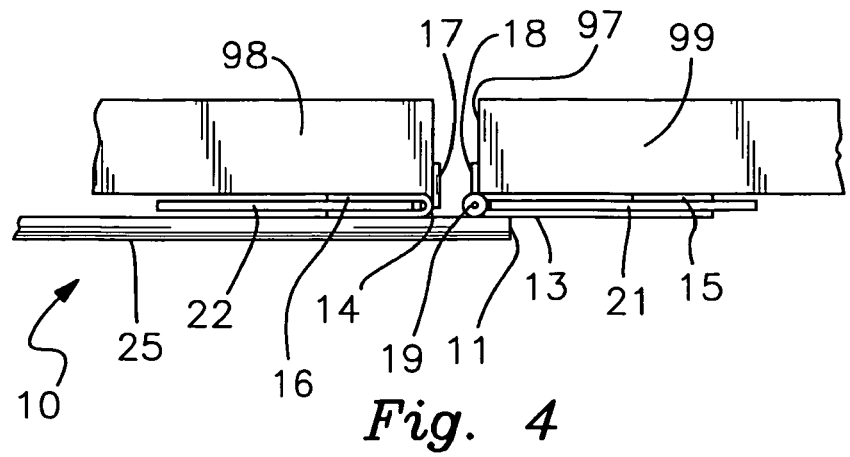
FIG. 4 is a partial side view of the invention as mounted at the osteotomy, with the abutment members abutting the edges of the bone osteotomy.

The proximal plate-mounting means 14 is provided with a relatively short, typically about 4 to 10 mm in length, abutment member 17 that is rigidly disposed on the distal end of the proximal plate-mounting means 14 generally perpendicularly to the axial direction and to the plane containing the bone plate 22, prior to any bending of the bone plate 22, such that it extends beyond the underside of the bone plate 22, the underside being the side of the bone plate 22 that will abut the bone segment 98. The abutment member 17, shown typically configured as a generally rectangular tab, arm or hook member, is positioned within the osteotomy gap 97 against the exposed end of the proximal bone segment 98 in order to transfer distractive force to the bone segment 98 when the separation distance between the distal plate-mounting means 13 and the proximal plate-mounting means 14 is increased, as shown in FIG. 4.

The distal plate-mounting means 13 is provided with a collapsible abutment member 18 of similar configuration to the fixed abutment member 17. Collapsible abutment member 18 is positioned on the proximal end of the distal plate-mounting means 13. During the distraction process, the collapsible abutment member 18 is oriented generally perpendicularly to the axial direction and to the plane containing the bone plate 21, prior to any bending of the bone plate 21, such that it extends beyond the underside of the bone plate 21, the underside being the side of the bone plate 21 that will abut the distal bone segment 99. The abutment member 18, shown typically configured as a generally rectangular tab, arm or hook member, is positioned within the osteotomy gap 97 against the exposed end of the distal bone segment 99 in order to transfer distractive force to the bone segment 99 when the separation distance between the distal plate-mounting means 13 and the proximal plate-mounting means 14 is increased. The collapsing abutment member 18 is provided with collapsing means 19, such as the hinge mechanism shown, such that the abutment member 18 is able to fold, pivot or bend toward the distal axial direction, preferably folding completely against or parallel to the bracket member 15, such that a small cross-sectional profile is presented in the axial direction.

Figure 5:
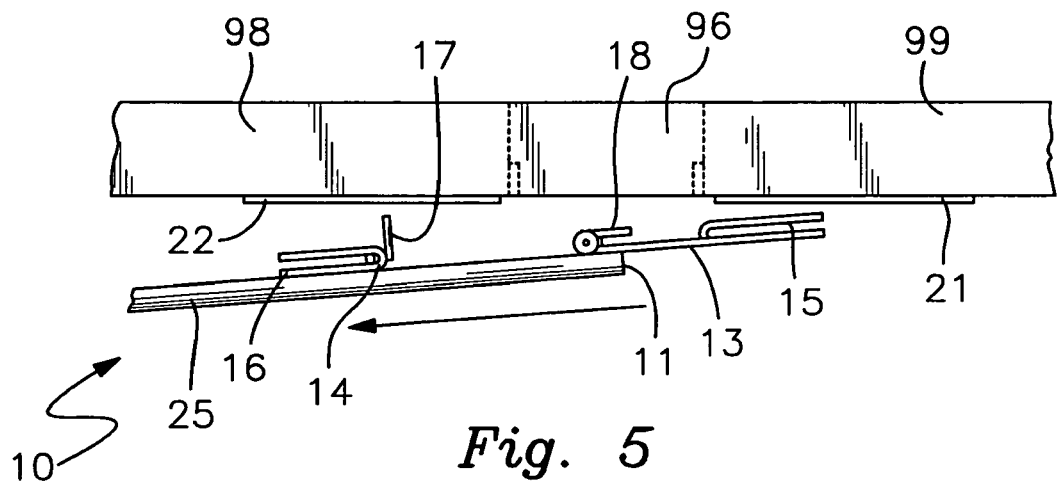
FIG. 5 is a partial side view of the invention as it is being withdrawn from the patient, such that the distal abutment member has pivoted to present a smaller profile during the extraction.

In this manner, when it is desired to remove the distractor means 10 from the patient after sufficient time has elapsed for the bio-resorbable material bone plates 21 and 22 to have weakened, the proximal end 12 is pivoted outward from the bone segment 98 such that the proximal plate-mounting means separates from the proximal bone plate 22 and its bone screws and such that fixed abutment member 17 of the proximal plate-mounting means 14 is withdrawn completely from the bone segment 98 and the regenerated bone 96, the distal end 11 of the distractor means 10 being used as a pivot member. This also results in the distal plate-mounting means 13 and collapsible abutment member 18 being pivoted away from the bone segment 99 and the regenerated bone 96, and in the distal plate-mounting means 13 being separated from the weakened distal bone plate 21 and its bone screws. After the distal plate-mounting means 13 has been moved a sufficient distance from the bone segment 99 for the abutment member 18 to clear the bone segment 99 and for the distal plate mounting means 13 to release from the distal bone plate 21, movement of the distractor means 10 and the distal plate-mounting means 13 in the proximal axial direction results in the collapse or pivoting of the collapsible abutment member 18 into the small profile configuration shown in FIG. 5 as the abutment member 18 encounters the surrounding tissue, thereby causing less damage to the tissue during the removal operation.

Figure 6:
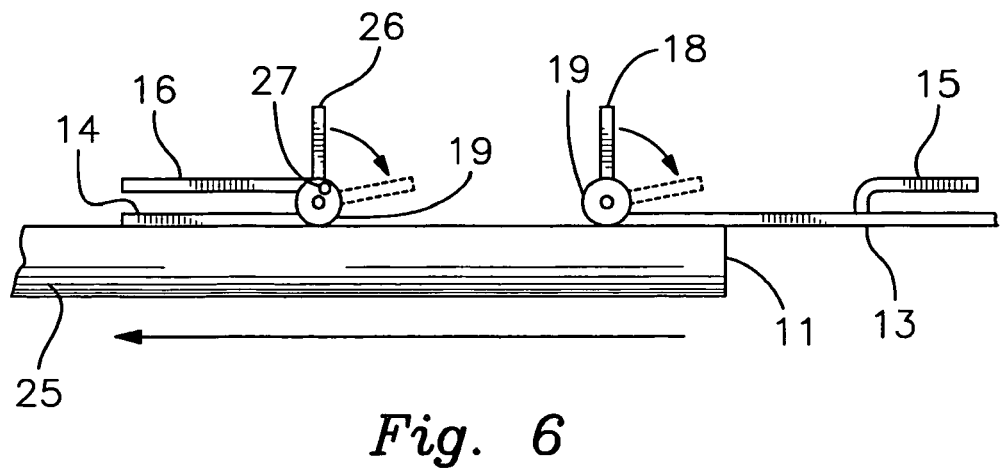
FIG. 6 is a partial view of an alternative embodiment for the invention, wherein both abutment members are collapsible.

In an alternative embodiment, as shown in FIG. 6, a releasable collapsible abutment member 26 of generally equivalent structure to the collapsible abutment member 18 is provided in place of the abutment member 17 located on the proximal plate-mounting means 14, such that the abutment member 17 likewise collapses or folds in the distal axial direction upon withdrawal of the proximal plate-mounting means 14 in the proximal axial direction. Such a structure, however, requires a locking or release mechanism 27, such as a removable pin for example, such that the abutment member 26 remains fixed in the perpendicular orientation during the distraction operation and cannot collapse in the distal direction until released by the physician.

It is contemplated that equivalent elements to those set forth above may be obvious to those skilled in the art, and therefore the true scope and definition of the invention is to be as set forth in the following claims.

I claim:

1. A bone distractor apparatus comprising:
    a proximal bone plate and a distal bone plate adapted to be affixed to bone;
    distractor means removably joined to said bone plates in a manner whereby operation of said distractor means increases the separation distance between said bone plates, said distractor means being separable from said proximal bone plate and said distal bone plate, such that said proximal bone plate and said distal bone plate remain affixed to bone when said distractor means is separated from said proximal bone plate and said distal bone plate;
    a collapsible distal abutment member joined directly to said distractor means and not to said distal bone plate, whereby said distal abutment member is collapsible only distally toward said distractor means.

2. The apparatus of claim 1, wherein said distal abutment member is joined to said distractor means by collapsing means.

3. The apparatus of claim 2, wherein said collapsing means comprises a hinge.

4. The apparatus of claim 3, wherein said bone plates are composed of bio-resorbable material.

5. The apparatus of claim 1, further comprising a distal plate-mounting means and a proximal plate-mounting means mounted to said distractor means, wherein said distal bone plate is joined directly to said distal plate-mounting means and said proximal plate member is joined directly to said proximal plate-mounting means, and further wherein said distal abutment member is joined directly to said distal plate-mounting means.

6. The apparatus of claim 5, wherein said distal abutment member is joined to said distractor means by collapsing means.

7. The apparatus of claim 6, wherein said collapsing means comprises a hinge.

8. The apparatus of claim 7, wherein said bone plates are composed of bio-resorbable material.

9. The apparatus of claim 1, further comprising a proximal abutment member joined to said distractor means.

10. The apparatus of claim 9, wherein said proximal, abutment member is collapsible toward said distractor means only in the distal direction.

11. The apparatus of claim 10, said proximal abutment member further comprising a locking release mechanism, such that said proximal abutment member is precluded from collapsing until released.

12. A bone distractor apparatus comprising:
    a proximal bone plate and a distal bone plate, both composed of a bio-resorbable material;
    a generally elongated distractor means joined to said bone plates in a manner whereby operation of said distractor means increases the separation distance between said bone plates;
    a distal abutment member joined to said distractor means by collapsing means and disposed generally perpendicularly to said distal bone plate, whereby said distal abutment member is collapsible toward said distractor means in the distal direction.

13. The apparatus of claim 12, wherein said collapsing means comprises a hinge.

14. The apparatus of claim 13, further comprising a distal plate-mounting means and a proximal plate-mounting means mounted to said distractor means, wherein said distal bone plate is joined directly to said distal plate-mounting means and said proximal plate member is joined directly to said proximal plate-mounting means, and further wherein said distal abutment member is joined directly to said distal plate-mounting means.

15. The apparatus of claim 13, further comprising a proximal abutment member joined to said distractor means.

16. The apparatus of claim 15, wherein said proximal abutment member is collapsible toward said distractor means.

17. The apparatus of claim 16, said proximal abutment member further comprising a locking release mechanism, such that said proximal abutment member is precluded from collapsing until released.

18. A bone distractor apparatus adapted to distract bone segments divided by an osteotomy gap, said apparatus comprising:
    a proximal bone plate adapted to be attached to a proximal bone segment on the proximal side of an osteotomy gap and a distal bone plate adapted to be attached to a distal bone segment on the distal side of an osteotomy gap, both bone plates being composed of a bio-resorbable material;
    a generally elongated distractor means removably joined to said bone plates in a manner whereby operation of said distractor means increases the separation distance between said bone plates, said elongated distractor means defining an axial direction, said distractor means being separable from said proximal bone plate and said distal bone plate, such that said proximal bone plate remains affixed to a proximal bone segment and said distal bone plate remains affixed to a distal bone segment when said distractor means is separated from said proximal bone plate and said distal bone plate;
    a distal abutment member joined to said distractor means by collapsing means and disposed generally perpendicularly to said axial direction, such that said distal abutment member extends into the osteotomy gap and abuts the distal bone segment, and whereby said distal abutment member comprises collapsing means whereby said distal abutment member is collapsible toward said distractor means in the distal axial direction.

19. The apparatus of claim 18, wherein said collapsing means comprises a hinge.

20. The apparatus of claim 18, further comprising a distal plate-mounting means and a proximal plate-mounting means mounted to said distractor means, wherein said distal bone plate is joined directly to said distal plate-mounting means and said proximal plate member is joined directly to said proximal plate-mounting means, and further wherein said distal abutment member is joined directly to said distal plate-mounting means.

21. The apparatus of claim 18, further comprising a proximal abutment member joined to said distractor means and disposed generally perpendicularly to said axial direction, such that said proximal abutment member extends into the osteotomy gap and abuts the proximal bone segment.

22. The apparatus of claim 21, wherein said proximal abutment member is collapsible toward said distractor means in the distal axial direction.

23. The apparatus of claim 21, said proximal abutment member further comprising a locking release mechanism, such that said proximal abutment member is precluded from collapsing until released.

* * * * *